United States Patent [19]

Stewart

[11] Patent Number: 4,718,411

[45] Date of Patent: Jan. 12, 1988

[54] MALE ERECTING DEVICE

[76] Inventor: Edward T. Stewart, 107 Plaza Ter., Dodge City, Kans. 67801

[21] Appl. No.: 14,361

[22] Filed: Feb. 13, 1987

[51] Int. Cl.⁴ .............................................. A61F 5/41
[52] U.S. Cl. ..................................................... 128/79
[58] Field of Search ................. 128/79; 604/347, 350, 604/146, 181; 417/553

[56] References Cited

U.S. PATENT DOCUMENTS

| | | | |
|---|---|---|---|
| 1,498,430 | 6/1924 | Doerfler | 128/79 |
| 2,614,565 | 10/1952 | Packer | 128/327 |
| 2,874,698 | 2/1959 | Sell | 128/79 |
| 3,421,504 | 1/1969 | Gibbons | 128/79 |
| 3,631,853 | 1/1972 | Burdette, Jr. | 128/79 |
| 3,744,486 | 7/1973 | Wilson | 128/79 |
| 4,175,554 | 11/1979 | Gerow | 128/79 |
| 4,378,008 | 3/1983 | Osbon, Sr. | 128/79 |

FOREIGN PATENT DOCUMENTS

| | | | |
|---|---|---|---|
| 148586 | 7/1985 | European Pat. Off. | 128/79 |
| 774558 | 10/1980 | U.S.S.R. | 128/79 |

*Primary Examiner*—Gene Mancene
*Assistant Examiner*—Cary E. Stone
*Attorney, Agent, or Firm*—John A. Hamilton

[57] ABSTRACT

A male erecting device including an open-ended penile tube adapted to be fitted over a non-erect penis and sealed against the torso around the base of the organ, and a vacuum pump operable to produce a vacuum within the tube, the vacuum normally producing an erection in many types of impotence. A specially designed vacuum regulating valve provides an accurate, finely adjustable limitation on the maximum vacuum which may be established in the penile tube, which is necessary for the safety and well being of the user, to prevent possible discomfort, pain or even damage to the penis. Valves are also provided for instantly relieving the vacuum entirely if the user should experience pain or discomfort, for relieving the vacuum automatically after a predetermined time to limit the exposure time of the penis to vacuum, and to disable the device completely for a further time period after cessation of the vacuum. The entire device is small, compact and entirely self-contained, requiring no connections for pneumatic or electric lines to any equipment remote from the device itself.

5 Claims, 4 Drawing Figures

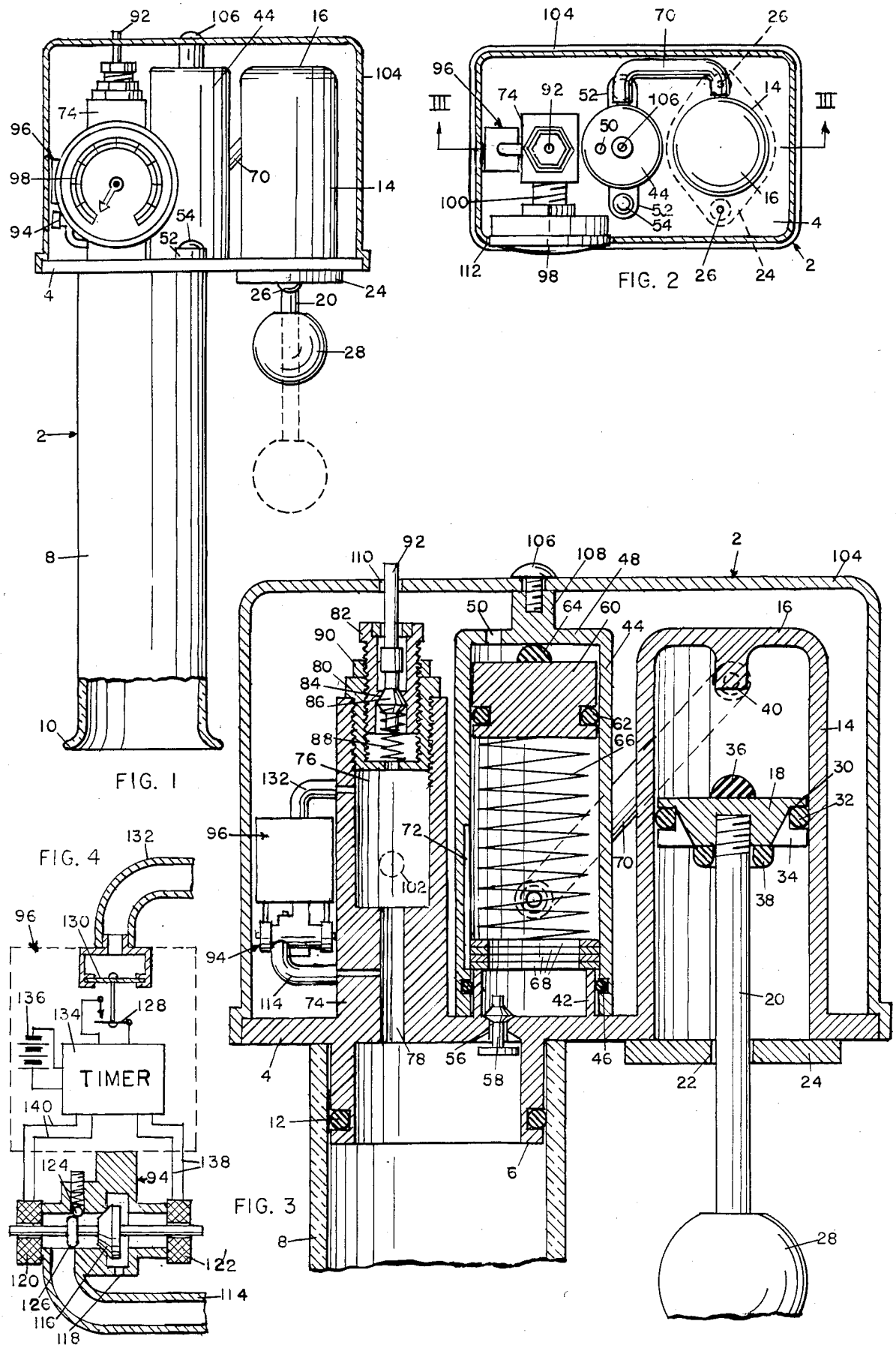

MALE ERECTING DEVICE

This invention relates to new and useful improvements in devices capable of assisting men to obtain good erection of the penis when for any reason, usually either physiological or psychological, they have difficulty in producing an erection in a normal manner. Generally, the device contemplated by the present invention consists of a tube, large enough to contain the erected penis but adapted to be sealed around the penis when it is not erect, and a pump operable to evacuate air from the tube to produce a partial vacuum around the penis. The vacuum allows the penis to lengthen and expand due to its own internal pressures, and this in turn allows a greater quantity of blood to enter and engorge the organ under normal blood pressures. The additional supply of blood produces an erection. In some cases, it may be necessary to apply an elastic constrictor band around the base of the penis, which may be applied either before or after the erection is produced, in order to maintain the erection after the erection is produced for a time sufficient to permit completion of a normal sex act, but the constrictor ring is not itself pertinent to the present invention, which is restricted to the vacuum-producing apparatus.

Applicant is well aware that devices of this general type are not new, but have been previously conceived in various forms, including forms including evacuable tubes to be applied over the penis, but all such prior devices within my knowledge have been subject to certain disadvantages and problems, especially in the areas of safety for the user and convenience of use. With regard to safety, no prior device of this type within my knowledge has any means for positively limiting the vacuum produced by the pump. Excessive vacuum can be injurious to the user in that it can cause rupture of blood vessels or internal tissues of the penis, or blistering of the skin, particularly of the sensitive glans. When the user is in sole control of the vacuum producing means, he may very well, either inadvertently or in the mistaken belief that "if a little is good, more must be better", operate said vacuum producing means to produce an execessive vacuum with its attendant dangers. The vacuum should be limited in accordance with competent medical advice, and the advice strictly adhered to. Accordingly, one object of the present invention is the provision of a device of the character described having means, not readily within the control of the user, for limiting the vacuum which may be applied to the penis.

The degree of vacuum which may safely be applied to the penis varies somewhat widely from individual to individual, and may vary from time to time even with a single individual, and it is accordingly another object of the present invention to provide means whereby the maximum vacuum producible by the vacuum pump may be adjusted. Since it is presently contemplated that the maximum variation required will fall within the range of vacuums equal to perhaps 7–9 inches of mercury, the adjustments must be small and accurate. Again, the adjustments should be made by means not readily within the control of the user, in order to prevent misuse.

Another distinct problem is the maintenance of suitable accuracy of the vacuum limit control. Commercially available vacuum relief valves, usually including steel balls spring-loaded to engage in steel valve seats, are rather notoriously inaccurate and inconsistent in their control particularly within the small range of vacuums useful in the present device, often varying as much as several inches of mercury in the vacuums they control from a presumed setting. Accordingly, still another object of the present invention is the provision of a device of the character described having a specially designed and novel vacuum regulating valve which is inherently extremely accurate, producing control usually within one-quarter of an inch of mercury.

Also, it has been found that exposure of the penis to vacuums for unduly long periods of time may be injurious to the user, even if the vacuum itself is within normally allowable limits. Accordingly, another object of the present invention is the provision of a device of the character described having means for relieving the vacuum automatically after it has been maintained for a predetermined period of time, also to be determined by medical advice.

It is also known that once the penis has been exposed to a vacuum, the process should not be repeated until after a predetermined longer period of time. Both exposure of the penis to vacuums for unduly long periods of time, and also the repeated exposure of the organ to vacuums after unduly short periods of time, produce symptoms much like those experienced by exposure of the organ to unduly high vacuums. Accordingly, another object of the present invention is the provision of means operable, after the organ has been subjected to a vacuum, and the vacuum has been relieved by the automatic time limiting means discussed above, to disable the device completely for a predetermined longer period of time, also to be determined by medical advice.

From the point of view of convenience of use, another problem with previous devices has been that they require the establishment of vacuum connections from the penile tube to remotely located vacuum pumps, or electrical connections for electrically operated vacuum pumps. The time and attention to detail required to make such connections may be psychologically disabling to the user, which is especially important in view of the fact that impotence of this type is often due to psychological problems of the user. Accordingly, still another object of the present invention is the provision of a device of the character described which is manually operated, and is entirely self-contained to be held in the hand of a user for convenient use, without "set-up" time.

Once an erection is produced by use of the present device, it is important that the penile tube be very quickly removable from the penis, especially in view of the fact that with many users, the erection may tend to be short-lived. Removal of the tube requires quick release of the vacuum if said removal is not to cause pain or discomfort to the user. Accordingly, another object of the present invention is the provision of a device of the character described having means whereby the tube vacuum may be relieved virtually instantaneously. This relief means is also useful in any stage of the use of the device, in order to relieve the vacuum if the user should experience pain or discomfort at any time, which indicates that use of the device should be discontinued.

Lack of the above features, particularly with regard to the provision of a positive limit to the vacuums applicable to the penis, and to adjustability of said vacuum limit, and to the accuracy of control of said vacuum limit, are important factors in the reluctance and even refusal on the part of many urologists and other medical authorities to prescribe or recommend, or even to condone, the use of vacuum devices for the treatment of male impotence.

With these objects in view, as well as other objects which will appear in the course of the specification, reference will be had to the accompanying drawing, wherein:

FIG. 1 is a side elevational view of a male erecting device embodying the present invention, with the cover shown in section to show the interior thereof, FIG. 2 is a top plan view of the device as shown in FIG. 1, FIG. 3 is an enlarged, fragmentary sectional view taken on line III—III of FIG. 2, and FIG. 4 is a schematic layout of the automatic vacuum relief system.

Like reference numerals apply to similar parts throughout the several views, and the numeral 2 applies generally to the device forming the subject matter of this invention. Such terms as "upward" and "downward", as used in this description, refer to the device as illustrated in the drawing, not to their position in actual use, which is indeterminate. The numeral 4 indicates a base plate, illustrated as generally rectangular and formed of metal, plastic or other suitable material, which carries all other elements of the device. A downwardly extending tubular neck 6 is formed integrally with the base plate, and has a tubular penile tube 8 fitted thereabout and projecting downwardly, being flared outwardly at its lower end as indicated at 10. It is large enough to contain the erected penis with air space remaining thereabout, and is preferably formed of transparent plastic in order that the penis may be visually observed therethrough. It is removable from the base plate for cleaning, and is sealed around neck 6 by a rubber O-ring 12. Parallel with tube 8 but transversely offset therefrom, a tubular vacuum pump cylinder 14 is formed integrally with base plate 4 and projects upwardly therefrom. Said cylinder is closed at its upper end by end wall 16 and opens downwardly through the base plate. A pump piston 18 is operably slidable in cylinder 14, and a piston rod 20 fixed in said piston extends downwardly below said base plate, being guided loosely in an orifice 22 formed therefor in a closure plate 24 affixed to the lower surface of said base plate by screws 26, and has a knob 28 affixed to its lower end, by means of which it may be reciprocated vertically, as indicated in dotted lines in FIG. 1, whereby to reciprocate the piston. The piston does not fit tightly in the cylinder, but has a generally square groove 30 formed in its cylindrical peripheral surface, in which a rubber O-ring 32 is mounted, said O-ring having dragging contact with the cylinder wall. The inner and lower walls of said groove are vented to the space below the piston by slots 34 cut in the piston. Thus when the piston is driven upwardly, the O-ring is dragged to the lower part of the groove and away from the top wall of the groove, and air can flow around the piston and through slots 34, but when the piston is pulled downwardly, the O-ring seals against both the top wall of the groove and the cylinder wall, and air cannot flow around the piston. The O-ring thus serves as a check valve, permitting only downward flow of air past the piston. Operation of the piston is cushioned, and the noise of operation reduced, by rubber bumpers 36 and 38 affixed respectively to the top and bottom of the piston and engageable respectively with a boss 40 formed on top cylinder end wall 16, and with closure plate 24.

Adjacent pump cylinder 14, and partially overlying penile tube 8, base plate 4 is provided with an integral upstanding neck 42, and the lower end of a regulating valve cylinder 44 is sealed about said neck by a rubber O-ring 46. Said cylinder is closed at its upper end by an end wall 48 having a venthole 50 formed therethrough, and is provided at its lower end with a pair of radially outwardly extending lugs 52 releasably affixed to base plate 4 by screws 54. A hole 56 formed through the base plate interconnects the interior of cylinder 44 with the interior of penile tube 8, said hole being controlled by a check valve 58, preferably formed of Neoprene or other semi-rigid material, which seats downwardly to prevent the flow of air from cylinder 44 to the penile tube, but is movable upwardly whenever the vacuum in cylinder 44 exceeds that in the penile tube to permit the upward flow of air. A regulating piston 60 is carried for operating sliding movement in cylinder 44, said piston being sealed therein by a rubber O-ring 62, and the noise of any contact of said piston with top end wall 48 being cushioned by a rubber bumper 64 fixed to the piston. Downward movement of the piston is yieldably resisted by a helical regulating spring 66 disposed in cylinder 44 and compressed between the bottom of piston 60 and a stack of flat, circular adjusting rings 68 supported on the upper end of base plate neck 42. The number of said rings used is variable, depending on the penile tube vacuum desired. The piston is moved downwardly against spring 66 by vacuum formed in cylinder 44 therebeneath, with atmospheric air pressure above the piston being maintained by air admitted through vent hole 50. A flexible vacuum hose 70 interconnects the upper end of pump cylinder 14, above the topmost position of piston 18, with regulating valve cylinder 44 beneath piston 60, so that operation of pump piston 18 will produce a vacuum below piston, 60. When piston 60 has been lowered to a predetermined distance, its O-ring 62 uncovers the upper end of a vertical groove 72 formed in the interior wall of the cylinder, and air is allowed to flow through said groove to relieve the vacuum beneath the piston.

Adjacent regulating valve cylinder 44, and also overlying penile tube 8, is an upstanding valve block 74, also formed integrally with base plate 4. Said valve body has an enlarged cavity 76 formed in the upper end portion thereof, interconnected with penile tube 8 through base plate 4 by a bore 78. Threaded into the upper end of cavity 76 is a tubular socket 80 into which a tubular valve body 82 is in turn threaded. Said valve body forms a valve seat 84 into which a valve member 86, also preferably formed of Neoprene or other semi-solid material is urged upwardly to close the valve by a spring 88. Said spring is compressed between the valve member and the base of socket member 80, and may be adjustably tensioned by screwing valve body 82 downwardly into the socket, the setting then being fixed by a lock nut 90. A spindle 92 is carried loosely in valve body 82, resting on valve 86, and projects upwardly, whereby to serve as a push-button, downward pressure on which will open valve 86 against the pressure of spring 88 to admit air to cavity 76, and thence through bore 78 to penile tube 8 to relieve any vacuum existing therein. Disposed adjacent valve block 74 is an automatic vacuum relief and control system including a valve 94 and timer 96, to be more fully described hereinbelow. A vacuum gauge 98 is provided with a stem 100 threaded into valve block 74. Said gauge is not shown in FIG. 3, but the position of its entry into valve block 74 is indicated generally by the dotted circle 102, and at all times it indicates the level of any vacuum existing in penile tube 8.

A hollow, generally rectilinear cover 104 is joined around its open side with base plate 4, and is of sufficient volume to completely enclose vacuum pump cylinder 14, regulating valve cylinder 44, valve block 74, and the vacuum relief and control system. It is secured releasably in position by a screw 106 extending through its top wall and threaded into a boss 108 formed on the top end wall 48 of cylinder 44. It is also provided with a hole 110 through which spindle 92 projects upwardly for manual operation, and a hole 112 in its forward wall through which vacuum gauge may project, or through which said gauge may be read.

As shown in FIG. 4, valve 94 is connected into passage 78 of valve block 74, whereby to be subject to the penile tube vacuum, by a conduit 114, and includes a valve plug 116 which may be either closed, as illustrated, whereby to seal conduit 114, or opened by movement to the right, as viewed, whereby to vent conduit 114 to atmosphere, through vent opening 118. It is closed by energization of a solenoid 120, and opened by energization of a solenoid 122. It is held releasably in either its closed position or in its open position by a spring-loaded detent ball 124, which engages a collar 126 on the valve stem. Timing device 96 includes a normally open electric switch 128 which is closed by an elastic diaphragm 130, said diaphragm being movable when a vacuum is induced in cavity 76 of valve block 74, to which it is interconnected by a conduit 132. Closure of switch 128 initiates operation of a timer unit 134 powered by a small electric battery 136. Said timer unit may be in the nature of a computer chip commonly used for driving digital electric alarm clocks, and is not deemed to require full and complete description here. Presuming that medical advice has determined that the user's penis should not be subjected to vacuum for more than three minutes, and that longer exposure would possibly be deleterious or dangerous, and that in no event should the organ again be subjected to vacuum any sooner than after the passing of an additional ten minute interval, timer 134 should be such that once its operation is initiated by closure of switch 128, it will, after a three minute interval, deliver a pulse of electric current to solenoid 122 through wires 138, whereby to open valve plug 116 to relieve the vacuum in penile tube 8, and after a further ten minute interval will deliver a pulse of electric current to solenoid 120 through wires 140 to close valve plug 116 to ready the device for re-establishment of a vacuum.

In operation, the flared open end 10 of penile tube 8 is applied over the non-erect penis, and sealed against the torso around the base of the organ. Petroleum jelly or the like may be used to facilitate the formation of an efficient seal. Pump piston 18 is then manually reciprocated by the use of knob 28, the piston allowing air to flow upwardly therearound on its upstroke, but functioning to seal in cylinder 14 and draw air through hose 70 from cylinder 44 below piston 60 on its downstroke, as previously described, whereby to form a partial vacuum below piston 60. Whenever this vacuum exceeds that in penile tube 8, check valve 58 opens and air is drawn from said tube to form a partial vacuum therein. On the following upstroke of piston 18, check valve 58 closes to seal the vacuum in tube 8. Repeated strokes of piston 18 will thus gradually increase the vacuum in tube 8, until a desired vacuum, pre-determined by competent medical advice, has been established in tube 8. The vacuum in cylinder 44 below piston 60 draws said piston downwardly against spring 66, until at the preset maximum vacuum, O-ring 62 of the piston passes below the upper end of groove 72 in the cylinder wall, whereupon air flows beneath the piston to relieve the vacuum. Check valve 58 will then remain closed, and no higher vacuum can be induced in penile tube 8. The specific vacuum to which the vacuum is limited is determined by the number of spacer rings 68 placed beneath spring 66. These rings pre-tension spring 66 to variable degrees, so as to vary the vacuum required to draw the piston downwardly sufficiently to uncover the upper end of groove 72. The greater number of rings inserted, the higher will be the vacuum permitted. The number of rings inserted should be determined by medical advice of a physician familiar with the condition of the user, and should not thereafter be changed except by additional advice of such physician. This adjustment is quite intentionally made rather obscure for the purpose of discouraging the user himself from changing the maximum vacuum to which his penis is subjected within tube 8. As shown, the adjustment requires the removal of screw 106 and cover 104, and then the removal of screws 54 and cylinder 44, before the number of rings 68 can be changed, and it is not likely that this would be readily apparent to the average user, nor would he be likely to have additional rings 68 to insert. The adjustment could be made by other means, for example by interchanging spring 66 for other springs having different moduli of elasticity, or by substituting cylinder 44 for others in which groove 72 rises to different heights, but the ring method shown is preferred. The specific form of the regulating valve shown has an important advantage over any other type of valve known to me. Prior valves available, usually consisting of a steel ball springloaded into a conical steel seat, are notoriously inaccurate and inconsistent in the vacuum levels they are capable of controlling, especially in view of the fact that the maximum range of vacuums allowable in devices of the present type, is perhaps only 7 to 9 inches of mercury. Such prior valves often allow a variation of several inches of mercury in the vacuums at which they will open. In the presently shown regulating valve, on the contrary, the greatly enlarged area of piston 60, plus the fact that said piston must travel through a relatively long stroke to open the valve, permit a very sensitive and reliably consistent control, spring 66 being relatively sensitive and selected to have a modulus of elasticity to yield the entire distance required to open the valve with a variation of vacuum equal to only about two inches of mercury. Extensive tests have shown that the present valve consistently maintains a vacuum within about one-quarter inch of mercury of the setting determined by the number of spacer rings 68 used. Thus each ring 68 may be of a thickness capable of increasing the control vacuum about one-quarter inch of mercury for each ring inserted. This degree of accuracy in the control of the vacuum, moreover, is essential to the safety and well-being of the user of the device, and the lack of such accuracy is one of the principal reasons many medical practitioners often refuse to prescribe or endorse the use of vacuum devices for this purpose.

As the penis present in penile tube 8 is subjected to the vacuum produced by the vacuum pump, the reduced air pressure around the organ permits it to enlarge and expand due to its own internal blood pressure. Tube 8 is rigid and sufficiently large that even when the penis is fully erect it does not fill said tube, so that the entire bulk of the organ is subjected to the vacuum. As the penis expands, the expansion reduces the internal pressure of the organ and thus encourages the flow of additional blood into the organ, thus engorging the organ with blood and producing a substantially normal erection. Tube 8 is then removed from the penis, and the erection desirably should last for a sufficient time for the user to complete a satisfactory act of sexual intercourse. The tube may be removed from the penis easily, and without pain or discomfort by manually pressing the outer end of spindle 92. This opens relief valve 86 against spring 88 to allow air to flow into penile tube 8 to relieve the vacuum therein virtually instantaneously. This relieves the vacuum "grip" of the flared end of the tube with the skin, so that the tube may be removed without discomfort. The tension of spring 88 is not critical, it being necessary only that said tension be sufficient to maintain valve 88 closed under the maximum vacuum which can be produced in the penile tube. If the user's impotence is such that he cannot maintain the erection for a time sufficient to permit completion of a satisfactory sex act after the tube is removed, it may be advantageous for him to apply an elastic constrictor ring around the base of the penis either before or after subjecting the organ to the vacuum. This restricts egress of blood from the organ, and thus assists in the maintenance of an erection. However, the constrictor ring is a standard device, and is not in itself a part of the present invention. The user may also press spindle 92 and remove tube 8 from the penis if, at any time during production or maintenance of vacuum in tube 8, he should experience pain or discomfort in the penis. Such pain or discomfort may indicate the beginning of injurious damage to the organ, and the user should be instructed to remove the tube in the event of any such pain or discomfort. Vacuum gauge 98 of course indicates the actual vacuum existing in penile tube 8 at all times, and hence may be used to check the operation of the pump and the various valves included in the device. Since its main practical use in this respect would be to guard against the possible establishment of excessively high vacuums in the penile tube, it would be desirable to color the portions of the gauge scale indicating excessive vacuums some warning color, such as red, to give clear visual warning of the excessive vacuum.

Not only do some users require different vacuums for effective treatment of their impotence, but also some users require different times of exposure to the vacuum, since their "response" or "reaction" times to produce an erection also vary. However, the exposure time should not be excessive, nor should re-establishment of the penile tube vacuum be permitted, once said vacuum has been terminated after any single use of the device, for a substantially longer time period, such for example by manual operation of pump piston 18, since either of these occurences may tend to produce pain, discomfort or possible damage similar to those caused by excessive vacuums. Accordingly, the automatic vacuum relief control provided by valve 94 and timer 96 is provided. The timer unit 134 is set in operation by the establishment of a vacuum in the penile tube, by the closure of switch 128. This should be set to initiate operation of the timer unit at a vacuum no higher than the minimum vacuum to be utilized in the penile tube. The timer unit, once its operation is initiated, will continue in operation until its operating cycle is completed. In the example given, it will then open valve 94 to vent the penile tube to atmosphere after a period of three minutes. If the vacuum has not produced an erection of the penis in that time, further exposure of the organ to vacuum will probably not be successful, and could in fact be injurious to the user. After an additional ten minute delay, the timer unit will again close valve 94 to ready the device for the re-establishment of a vacuum in the penile tube, and operation of the timer unit will cease, whereby it is readied for reactuation by another closure of switch 128. Of course, timer units 134 could be selected to provide other time delays, depending on medical advice. The timer unit could also be of a type which is adjustably settable to allow setting thereof to different time delays. However, the preset type of timer is preferred, since it further removes control of the device from the user himself, and since this is desired in view of the fact that his judgment might readily be erroneous.

While I have shown and described a specific embodiment of my invention, it will be readily apparent that many minor changes of structure and operation could be made without departing from the spirit of the invention.

What I claim as new and desire to protect by Letters Patent is:

1. A male erecting device comprising a self-contained, hand-held unit, said unit comprising:
    a. a penile tube sufficiently large to contain a fully erect penis therein, being open at one end to be applicable over a non-erect penis and to be sealed against the user's body around the base of the penis,
    b. a vacuum pump operable when actuated to pump air from said penile tube to produce a vacuum therein, said vacuum being operable to cause erection of the penis, said pump being manually operable and comprising a pump cylinder, a manually operable piston movable in said cylinder, said cylinder being vented to atmosphere at one side of said piston and being connected to said penile tube at the opposite side of said piston, and
    c. a check valve carried by said piston and operable to permit the flow of air past said piston toward the vented side thereof, but to close to prevent a reverse flow of air, said check valve comprising a rubber O-ring contained loosely in a peripheral groove of said piston and having wiping contact with the wall of said cylinder, said groove being vented to the cylinder at the vented side of said cylinder, said O-ring functioning as a valve to close the air passage around the piston during the vacuum stroke of said piston, but to open said air passage during the reverse stroke of said piston.

2. A male erecting device comprising a self-contained, hand-held unit, said unit comprising:
    a. a penile tube sufficiently large to contain a fully erect penis therein, being open at one end to be applicable over a non-erect penis and to be sealed against the user's body around the base of the penis,
    b. a vacuum pump operable when actuated to pump air from said penile tube to produce a vacuum therein, said vacuum being operable to cause erection of the penis,
    c. a check valve operable to allow air to pass from said penile tube to said pump, but to close against reverse movement of said air, and
    d. a vacuum regulating valve interposed between said vacuum pump and said penile tube, and automatically operable to limit the vacuum producible in said penile tube to a predetermined maximum level said vacuum regulating valve comprising a cylinder of substantial cross-sectional area, a piston operable in said cylinder, and operable by an extended movement thereof in one direction to vent said cylinder to atmosphere, said vacuum pump being interconnected into said cylinder at the side of said piston toward which said piston moves in said one direction, whereby the pump vacuum moves said piston in said one direction, and resilient means yieldably resisting movement of said piston in said one direction.

3. A male erecting device as recited in claim 2 with the addition of means operable to adjust the effective tension of said resilient means.

4. A male erecting device as recited in claim 3 wherein said resilient means comprises a spring compressed between said piston and a fixed base, and wherein said adjusting means comprises a variable number of spacer members interposed between said fixed base and said spring.

5. A male erecting device comprising a self-contained, hand-held unit, said unit comprising:

a. a penile tube sufficiently large to contain a fully erect penis therein, being open at one end to be applicable over a non-erect penis and to be sealed against the user's body around the base of the penis, b. a manually operable vacuum pump operable to pump air from said penile tube to produce a vacuum therein, said vacuum being operable to cause erection of the penis, c. a check valve operable to allow air to pass from said penile tube to said pump, but to close against reverse movement of said air, d. a vacuum relief valve operable when closed to seal the closed end of said penile tube against the entry of air, and when open to vent said penile tube to atmosphere, e. timer means operable upon actuation to complete a cycle in which it first opens said relief valve after a pre-determined time lapse, closes said relief valve after a pre-determined additional time lapse, and then comes to rest until again actuated, and f. means operable to actuate said timer means responsively to the establishment of a vacuum in said penile tube.

* * * * *